United States Patent [19]

Gibbons et al.

[11] Patent Number: 5,068,198

[45] Date of Patent: Nov. 26, 1991

[54] LIQUID SINGLE REAGENT FOR ASSAYS INVOLVING CONFINING GELS

[75] Inventors: Ian Gibbons, Sunnyvale; Edwin F. Ullman, Atherton; Philip L. Felgner, Los Altos, all of Calif.

[73] Assignee: Syntex (U.S.A.) Inc., Palo Alto, Calif.

[21] Appl. No.: 298,192

[22] Filed: Jan. 13, 1989

Related U.S. Application Data

[63] Continuation of Ser. No. 844,910, Mar. 26, 1986, abandoned.

[51] Int. Cl.$^5$ .................................... G01N 33/549
[52] U.S. Cl. .................................... 436/535; 435/7.1; 435/7.2; 435/7.5; 436/519; 436/520; 436/522; 436/529; 436/531; 436/829
[58] Field of Search ............... 436/829, 519, 520, 522, 436/531, 535

[56] References Cited

U.S. PATENT DOCUMENTS

| | | |
|---|---|---|
| 3,850,578 | 11/1974 | McConnell . |
| 4,235,792 | 11/1980 | Hsia et al. ............... 436/829 |
| 4,255,411 | 3/1981 | Lim et al. ............... 436/829 |
| 4,311,712 | 1/1982 | Evans et al. . |
| 4,483,921 | 11/1984 | Cole . |
| 4,483,929 | 11/1984 | Szoka . |
| 4,485,054 | 11/1984 | Mezei et al. . |
| 4,522,803 | 6/1985 | Lenk et al. . |
| 4,529,561 | 7/1985 | Hunt et al. . |
| 4,622,294 | 11/1986 | Kung et al. . |
| 4,752,572 | 6/1988 | Sandberg ............... 436/829 |
| 4,971,916 | 11/1990 | Jou et al. ............... 436/512 |

FOREIGN PATENT DOCUMENTS

| | | |
|---|---|---|
| EP-A-0092453 | 10/1983 | European Pat. Off. . |
| EP-A-0171946 | 2/1986 | European Pat. Off. . |
| GB-A-2069133 | 8/1981 | United Kingdom . |
| WO-A-8402579 | 7/1984 | World Int. Prop. O. . |
| WO-A-8604682 | 8/1986 | World Int. Prop. O. . |

OTHER PUBLICATIONS

Litchfield et al., "High Sensitive Immunoassays . . .", *Clin. Chem.*, 30, 1441–1445 (1984).
Gregoriadis et al., Biochemical and Biophysical Research Communications, pp. 537–544 (1975).
Sukoyan et al., Mol. Gen. Genet., 201(3), pp. 487–491 (1985).
Patel, FEBS Letters 62(1), pp. 60–63 (1976).
Clinical Chemistry, vol. 30, No. 9, 1984, pp. 1441–1445, W. J. Litchfield et al., "Highly Sensitive Immunoassays Based on Use of Liposomes Without Complement".

*Primary Examiner*—Sam Rosen
*Attorney, Agent, or Firm*—Shelley G. Precivale; Carol F. Barrett; Gerald F. Swiss

[57] ABSTRACT

Assay methods and compositions are provided for determining an analyte in a sample suspected of containing the analyte. The composition comprises in a novel single liquid reagent at least one specific binding pair (sbp) member and its complementary member wherein at least one sbp member is reversibly confined in a material that temporarily renders the confined sbp member incapable of binding with its complementary sbp member. At least one of the sbp members is bound to a member of a signal producing system capable of producing a detectable signal in relation to the amount of analyte in the sample. The confinement is reversed, any remaining members of the signal producing system are added, and the signal produced in relation to the amount of analyte is measured. Examples of the confining material are lipid bilayers, cells and gels.

71 Claims, No Drawings

LIQUID SINGLE REAGENT FOR ASSAYS INVOLVING CONFINING GELS

This is a continuation of pending application Ser. No. 844,910, filed Mar. 26, 1986, now abandoned.

BACKGROUND OF THE INVENTION

1. Field of the Invention

There is continuing need for simple rapid and accurate qualitative and quantitative determinations of biologically active substances. There is a need for methods that can be conducted by technicians with a low level of skill. In addition there is a need for convenience, reliability and simplicity. In clinical laboratories, there is increasingly a desire for simpler assays that require use of as few reagents and as few steps as possible.

Immunoassays usually employ more than one reagent. In most cases, the reagents cannot be combined in a liquid medium prior to running the assay because they contain components that would react on contact with each other. It is desirable to find a method to combine the active materials in liquid form while preventing the reagents from reacting with each other until such time as a means for releasing one or more of the reagents is provided. Generally in immunoassays the reagents are members of a specific binding pair, consisting of ligand and its complementary receptor, one of which is labelled with a member of a signal producing system. Specific binding pair members that are complementary to each other usually react upon contact. Therefore, such reagents are generally stored separately until just prior to the time an assay is conducted.

One patented technique for combining interreactive agents in a single reagent is to formulate the reagents dry so that no reactions occur until a liquid sample or diluent is added. Dry reagents, however, impose some restraints on assay methods. Achieving a homogeneous blend and avoiding water uptake are matters of concern. Further, premature reaction must be avoided. Dry reagents are expensive and their manufacture and quality control are difficult. For example, it is generally necessary to add the sample and a diluent simultaneously and shake vigorously to assure full dissolution of the powder before the reaction has progressed significantly. Additionally, special processing devices are required.

It is, therefore, desirable to develop a new assay method for determining an analyte in a sample wherein two or more specific binding members are combined in a liquid single reagent. Such a reagent avoids the need for dry reagent blending and shaking and does not require simultaneous addition of sample and diluent. A single liquid reagent decreases the time and skill needed to perform an assay.

2. Description of the Related Art

Litchfield et al., "High Sensitive Immunoassays Based on Use of Liposomes without Complement," *Clin Chem* 30, 1441–1445 (1984) discuss a liposome-based immunoassay using covalently linked hapten-cytolysin conjugates to lyse vesicles with entrapped enzymes. U.S. Pat. Nos. 3,850,578; 4,483,921; and 4,483,929 disclose immunoreactive liposome reagents in which antigen or antibody is bound to the surface of lipid vesicles. A variety of methods for preparing lipid vesicles are known; see for example, U.S. Pat. Nos. 4,529,561, 4,522,803 and 4,485,054. U.S. Pat. No. 4,311,712 discloses a process for preparing a freeze-dried, liposome mixture.

SUMMARY OF THE INVENTION

Methods and compositions are provided for determining the presence of an analyte that is a member of a specific binding pair (sbp)—ligand and its complementary receptor—in a sample suspected of containing the analyte. The method is carried out using a composition that includes complementary sbp members in a single liquid medium wherein at least one sbp member is reversibly confined in a material that renders the member temporarily incapable of binding with its complementary sbp member. The confining material is either a synthetic or a natural vehicle. At least one of the sbp members is bound to a member of a signal producing system. Means for reversing the confinement of the temporarily confined sbp member is provided for combining with the liquid medium at the appropriate time. Chemical or physical means or a combination thereof are used to reverse the confinement of the temporarily confined sbp member. In the method, the reagents including those mentioned above are combined in appropriate order and the signal produced in relation to the amount of analyte in the sample is measured.

The method of the invention provides a way for supplying normally interreactive sbp members in a single liquid reagent. Because at least one of the sbp members is temporarily confined, the single liquid reagent can be prepared in premeasured quantities at the manufacturing site and then shipped to the user and stored for future use without need to measure or blend individual reagents.

The method finds particular use in various immunoassay techniques including spin immunoassay, FIA, EMIT, ELISA, RIA, and chemiluminescent immunoassays. The method is also useful in particle agglutination immunoassays in which one of the sbp members is not on a particle.

A kit that includes the single liquid reagent is provided for use in assays. A means for reversing the confinement of the temporarily confined sbp member and ancillary agents can also be provided in the kit.

DESCRIPTION OF THE SPECIFIC EMBODIMENTS

The present invention relates to a method of combining specific binding reagents in a single liquid medium in a manner which temporarily delays reaction between the reagents. The method involves encapsulating one reagent as a means for rendering the reagent temporarily non-reactive with the other reagents followed by specific release of the entrapped material at a prescribed time. The encapsulated reagent and the other reagent or reagents are present in a liquid medium. A sensitive, accurate and simplified assay method is provided utilizing the above liquid medium for determining a wide variety of analytes in a sample suspected of containing the analyte.

In accordance with the subject invention, an assay method and composition are provided for determining the presence of an analyte that is a member of a specific binding pair (sbp) consisting of ligand and its complementary receptor. The sample suspected of containing the analyte is combined with a composition that includes in a single liquid medium at least (1) one sbp member reversibly confined in a material that temporarily renders the confined sbp member incapable of binding with its complementary sbp member and (2) the complementary sbp member. At least one of the sbp members is bound to a member of a signal producing system. Other members of the signal producing system may also be present in the single liquid medium. In some cases, these additional members of the signal producing system are encapsulated with the sbp member. Alternatively, additional members of the signal producing system may be in a separate medium.

Before proceeding further with the description of the specific embodiments of the present invention, a number of terms will be defined.

Analyte—the compound or composition to be measured, the material of interest. The analyte can be a member of a specific binding pair (sbp) and may be a ligand, which is mono- or polyvalent, usually antigenic or haptenic, and is a single compound or plurality of compounds which share at least one common epitopic or determinant site.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which include morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfonamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand—any organic compound for which a receptor naturally exists or can be prepared.

Receptor (antiligand)—any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids and the like.

Label—A member of the signal producing system that is conjugated to an sbp member. The label can be isotopic or non-isotopic, usually non-isotopic, including catalysts such as an enzyme, a chromogen such as a fluorescer, dye or chemiluminescer, a radioactive substance, a particle, and so forth.

Signal Producing System—The signal producing system may have one or more components, at least one component being a label. The signal producing system generates a signal that relates to the presence or amount of analyte in a sample. The signal producing system includes all of the reagents required to produce a measurable signal. At least one member of the signal producing system is bound to at least one sbp member. Other components of the signal producing system can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of radioactivity, the degree of aggregation of particles or electromagnetic radiation, desirably by visual examination. For the most part, the signal producing system will involve a chromophoric substrate and enzyme, where chromophoric substrates are enzymatically converted to dyes which absorb light in the ultraviolet or visible region, phosphors, fluorescers or chemiluminescers.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and co-enzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively, luciferases may be used such as firefly luciferase and bacterial luciferase.

Illustrative co-enzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure in incorporated herein by reference.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Material for reversibly confining an sbp member—Any material can be employed that is capable of confining an sbp member temporarily so as to prevent the confined sbp member from binding to its complementary sbp member. For example, the prevention of the binding may be due to the inhibition of access of the sbp members to one another. The confinement must be reversible. The material will usually be finely divided to permit it to be suspended in a liquid medium and to provide for rapid release of the confined sbp member. The particles may be spherical or irregularly shaped, and will normally have average diameters of 10 nm to 500μ, more usually 20 nm to 2μ, frequently 100 nm to 1μ. The materials will be compatible with and insoluble in the liquid medium, usually an aqueous buffer solution, and will be comprised of an immissible liquid, liquid crystal, solid, gel, or the like, wherein "immissible" means immissible under the conditions of storing the confined sbp number but not necessarily under the assay conditions. Illustrative materials include lipid bilayers such as liposomes, artificial cells, vesicles, natural cell membranes such as red blood cells ghosts; gels such as gelatin and agarose; polymerized beads and the like.

Liposomes are microvesicles of approximately spherical shape. The outer shell of a liposome consists of a phospholipid bilayer that encloses a volume of water or an aqueous solution. Liposomes with more than one bilayer are referred to as multilamellar vesicles. Liposomes with only one bilayer are called unilamellar vesicles. The bilayer acts as an impermeable barrier to diffusion of a complementary sbp. The phospholipids in the bilayer may be replaced in whole or in part with other amphiphylic compounds that have a polar head group, usually charged, and a hydrophobic portion usually comprised of two or more linear hydrocarbon chains. Examples of phospholipid substitutes include dicetylphosphate, dialkoxypropylphosphates wherein the alkyl groups have linear chains of 12-20 carbon atoms, DOTMA, as disclosed in U.S. patent application Ser. No. 811,146 filing Dec. 19, 1985, which is hereby incorporated by references herein, sphingomyelin, cardiolipin, and the like.

For use in the present invention the liposomes must be capable of housing the sbp member. Generally, the liposomes are at least about 20 nm to 2μ, usually about 100 nm to 1μ, preferably about 200-600 nm. Preferred liposomes are those of a size that disperse readily to give a uniform suspension that settles very slowly and that are large enough to encapsulate a substantial quantity of sbp member or remains homogeneous. The liposomes of the present invention, in contradistinction to past methods, are formed so that the outer surface of the lipid vesicle is substantially free of sbp members.

Liposomes may be produced by hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is useable as a final step during the production of the liposomes. U.S. Pat. No. 4,529,561 discloses a method of extruding liposomes under pressure through a uniform pore-size membrane to improve size uniformity.

The phospholipids of the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-α-palymitoyl oleoylphosphatidylcholine (POPC), palmitoyl oleoylphosphatidyl glycerol (POPG), L-α-dioleoylphosphatidylglycerol, and L-α-(dioleoyl)-phosphatidyl ethanolamine.

The liposome can also include cholesterol and its derivatives and a variety of amphiphiles in the bilayer.

Exemplary of preferred liposomes in accordance with the present invention are those composed of 65-97% by weight POPC, 3-30% by weight POPG, and 0-30% by weight cholesterol. In a particularly preferred embodiment, the composition of the liposomes is 67-76% POPC, 3-4% POPG, and 20-30% cholesterol.

Liposomes, as indicated above, can be prepared in a variety of methods. An illustrative method involves combining the phospholipid in a chloroform solution and then removing the chloroform under a stream of nitrogen. Remaining traces of solvent can be removed, for example, using high vacuum. The phospholipid is then dissolved in a freezable solvent such as t-butanol or cyclohexane with gentle mixing, and the solution is then freeze-dried. The resultant powder is kept dry and cold until used to encapsulate an sbp member.

The material to be encapsulated is dissolved in buffer. Illustrative buffers include borate, phosphate, carbonate, Tris, barbital, and the like. The particular buffer employed is not critical to this invention; however, in individual encapsulations one buffer may be preferred over another.

A liposome suspension can be produced by mixing the lipid powder and the material to be encapsulated. The suspension is then diluted with buffer and filtered through a succession of filters with progressively smaller pores. For example, 1.0μ, 0.6μ, 0.4μ, and 0.2μ. Repeated filtration through any of the filters, and in particular through the smallest filter, is desirable. The liposomes can be purified by, for example, gel filtration, such as through a column of Sephacryl S-1000. The column can be eluted with buffer and the liposomes collected.

In a preferred embodiment, at least one of the reversibly confined sbp members is bound to a member of the signal producing system. In such a case, the reversibly confined member can be, for example, a conjugate of an enzyme and a hapten, the complementary member, which may also be reversibly confined or may be free, can be, for example, antibody for the hapten, and the confining material can be, for example, a liposome. In those cases where the confined material is a conjugate of an enzyme and a hapten, the encapsulated material may optionally include a stabilizer for the enzyme. One advantage of encapsulating the enzyme is that stabilizing agents can be included in the encapsulated material at much higher concentrations than would otherwise be practical in the bulk solution where they could adversely affect assay performance. Thus, encapsulation provides an opportunity to achieve greater enzyme stability than would be possible in a bulk solutin when there are limitations concerning the composition of the bulk solution such as viscosity, ionic strength, pH, and the concentration of enzyme inhibitors.

Alternatively, the reversibly confined member can be an unlabeled sbp member, for example, an antibody and the complementary member can be a conjugate of a label such as an enzyme and an sbp member such as a hapten.

Where the material for reversibly confining the sbp member is a red blood cell ghost, the sbp member can be incorporated in the cells in accordance with known techniques such as that described in *Method in Enzymol-*

*ogy*, Vol. XXXI, ed. S. Fleischer and L. Packer, pgs 172-180, Acad. Press (1974).

It is also within the scope of the present invention to reversibly confine more than one sbp member, where the confined sbp members are present in the same liquid medium.

Means for Reversing Confinement—An sbp member is reversibly confined when it is incapable of reacting with its complementary sbp under conditions where the two sbp member members are stored in the same liquid medium, but becomes capable of reacting with its complementary sbp member by the addition of a means for reversing confinement. Any chemical compound, composition, or material, either naturally occurring or synthetic, organic or inorganic, or any physical means or combination thereof or any enzymatic method or lytic protein material can be used that is capable of reversing the confinement of the temporarily confined sbp member provided it does not substantially interfere with the assay performance. The means for reversing confinement will depend on the material used for reversibly confining the sbp member.

Exemplary chemical compounds, compositions or materials for reversing confinement within liposomes and cell membranes include detergents including TRITON, sodium deoxycholate, octylglucoside, sodium dodecylsulfate and the like. Confinement by phospholipid liposomes and cell membranes can be reversed with polypeptides such as melittin, enzymes such as phospholipase, multicharged metal ions such as $Cu^{++}$ and $Mg^{++}$. Cell membranes will release their contents by osmotic shock. Liposomes, cell membranes, and gels can release their contents by sonication or by thermal changes, usually heating. Calcium alginate forms a gel that is dissolved by agents that chelate calcium ion such as EDTA. The above materials and their preparation or isolation are well-known in the art and many are commercially available.

Illustrative physical means for reversing confinement include change in temperature, including freezing and thawing, sonication, and osmotic shock.

As previously indicated, the present invention involves a single liquid reagent and its use in assays. The assays can be homogeneous or heterogeneous and can involve a label that is catalytic, chromophoric, radioactive, and so forth. The single liquid reagent of the present invention is particularly useful in the method described in U.S. Pat. No. 3,817,837. Other methods in which the present reagent can be employed include, by way of example not limitation, those described in "Enzyme-Immunoassay," by Edward T. Maggio, CRC Press, Inc., Boca Raton, Fla., 1980, and U.S. Pat. Nos. 3,690,834; 3,791,932; 3,850,578; 3,853,987; 3,867,517; 3,901,654; 3,935,074; 3,984,533; 3,996,345; and 4,098,876.

The method of the invention generally comprises combining a sample suspected of containing an analyte in a single liquid medium which includes (1) at least one sbp member that is reversibly confined in a material that renders the sbp member temporarily incapable of binding with its complementary sbp member, and (2) the complementary sbp member. At least one of the sbp members is bound to a member of a signal producing system. The substance reversibly confined will frequently be a labeled sbp member such as an enzyme-drug conjugate. In such a case, the non-confined sbp member is the complementary sbp member such as antibody for the drug. Because of the permeability barrier presented by the material encapsulating the reversibly confined sbp member, the complementary sbp member cannot react with the confined member.

In carrying out the assay method, a predetermined amount of a sample suspected of containing the analyte is measured. The amount of sample will generally be chosen so as to result in an accurate and sensitive assay for the analyte. Generally, for many drugs in physiological fluid, the volume will range from about 1.0 to 500 $\mu l$, usually about 5 to 100 $\mu l$. Depending on the nature of the sample and initial volume, the sample can be diluted with an appropriate volume of distilled or deionized water or buffer. Normally, the sample is combined with the liquid reagent composition of the invention and subsequently means for reversing the confinement is provided. The amount of liquid reagent employed will depend on the amount of dilution of the sample required to avoid non-specific interference from sample components, the concentration range of the analyte, and consideration of factors such as the optimum volume for accurate liquid measurements and spectrometric determination. Usually, the amount of liquid reagent will be 5 $\mu l$ to 3 ml, frequently 25 $\mu l$ to 1 ml. The final volume of the combination will be about 5 $\mu l$ to 3 ml, usually about 50 to 500 $\mu l$. As mentioned above, at least one member of the signal producing system is bound to one of the sbp members. In the method, the medium can also contain additional members of the signal producing system, which can be present initially separate from or within the confined material or both. The concentration of the various members of the signal producing system will vary and be dependent upon the concentration range of the analyte of interest.

The amount of the means for reversing the confinement employed will be dependent on the nature and amount of the material for reversibly confining the sbp member, the nature of releasing agent and the rate of release desired. When a chemical releasing agent or a combination of chemical agents is employed, the concentration of the agent or agents should be sufficient to result in substantial or complete release of the confined sbp member within the desired time. Generally it will be convenient to cause complete release in less than 5 minutes, preferably less than 1 minute, more preferably in less than 15 seconds. Frequently, release will occur essentially instantaneously upon providing the means for reversing confinement.

When detergents are used as the means for reversing confinement, the amount and composition of the detergent will be selected empirically to maximize the amount of sbp member released and minimize the release time. Where enzymes or protein reagents are used, the cost and availability of these reagents will be important factors in determining how much of these reagents can be used. In general, the more of these reagents that are used, the faster and more complete will be the releasing process. With these and other means for reversing confinement, a limitation on the amount of the reagent, where chemical, and the magnitude of the process, where physical, will be the need to avoid any adverse affects on the assay components or assay result. It is important to choose the releasing agent or agents with regard to the nature of the encapsulating material and the sbp members to minimize or avoid damage to the sbp member and its complementary member after the release of the sbp member from encapsulation.

After the sample containing the analyte has been combined with the liquid medium and the means for reversing the confinement of the confined sbp member has been provided, the liquid medium is held for a period of time sufficient for the binding to occur. Normally, this requires at least about 5 seconds to about 30 minutes, and more usually about 10 seconds to 5 minutes. Thereafter, the first reading of a detectable signal is taken. Any further readings will normally be taken about 30 seconds to 60 minutes after the time of mixing.

Moderate temperatures are normally employed for carrying out the method and usually constant temperatures during the period for conducting the method. Generally, the temperature for the method will range from about 0° to 50° C., more usually from about 15° to 40° C. After the reversal of the encapsulation of the sbp member is accomplished, a temperature that promotes binding of the sbp member and its complementary member is chosen. Again, moderate temperatures are generally employed for carrying out an assay and usually constant temperatures. The temperatures for the determination will generally range from about 10° to 50° C., more usually from 15°-40° C.

In carrying out the method the pH for the medium will usually be in the range of 2 to 12, more usually in the range of about 5 to 10, and preferably in the range of about 6 to 9. The pH is chosen so as to prevent reversal of confinement, to control the stability of the reagents and to prevent unwanted reactions during storage. Where the pH of the medium is not suitable for carrying out the assay, a suitable buffer will be added to the medium prior to or simultaneously with addition of the means for release to provide a pH that will permit the assay to be carried out. Various buffers may be used to achieve the desired pH and to maintain the pH during the determination. The particular buffer employed is not critical to this invention, but in individual assays, one buffer may be preferred over another. Illustrative buffers include borate, phosphate, carbonate, Tris, barbital and the like.

In addition to performing an assay for the analyte, it will normally be desirable to perform assays with one or more calibrators, whereby one would obtain either a single value or a plurality of values at different concentrations and graph the concentration of analyte versus the observed values to obtain a standard curve. No specific temperature control is required, as long as the calibrators and the analyte assay determinations are carried out under substantially similar ambient conditions.

The present method has particular advantages for automated assay procedures by providing a way to provide a single liquid reagent containing both an sbp member and its complementary member at least one of which is bound to a signal producing system. The present invention makes it unnecessary to measure and mix separate liquid reagents to the correct proportions prior to performing the assay or to reconstitute solid reagents.

Illustrative of a method of performing an assay using the single liquid reagent of the present invention is disclosed in U.S. Pat. No. 3,817,837. The reversibly confined material can be an enzyme-hapten conjugate such as, for example, glucose-6-phosphate dehydrogenase-theophylline; the complementary member can be unconfined and be antibody for the analyte, for example, anti-theophylline and the confining material can be a liposome. The single formulation and the analyte are combined.

In such a method the assay protocol is initiated by employing means for reversing the confinement of the enzyme conjugate. Thus, a detergent such as TRITON X-100 or sodium deoxycholate, or a polypeptide, such as, for example, melittin, can be added to the liquid medium. Alternatively, a physical means including a change in temperature, sonication or osmotic shock may be used.

After the temporary confinement of the single liquid formulation containing the liposome-confined enzyme-hapten conjugate and the antibody, is reversed and any additional signal producing system reagents are added, such as enzyme substrates, the enzymatic activity of the assay medium is determined and related to the concentration of the analyte in the medium. The enzyme-hapten conjugate and the analyte will compete for the antibody. Since the enzymatic activity will be changed, usually diminished or inhibited, when the enzyme-hapten conjugate binds to the antibody, the enzymatic activity of the solution will be directly related to the amount of analyte present in the assay medium. Preferably, the enzyme and enzyme substrate are selected so that either the substrate or the end product absorbs light in the ultraviolet or the visible region or fluorescer. Therefore, upon reversing the confinement of the single test liquid reagent of this invention in the aqueous solution containing the analyte one can determine the analyte concentration by measuring the absorption or emission of light.

The invention further comprises a composition comprising in a liquid medium (a) at least one sbp member reversibly confined in a material rendering the sbp member temporarily incapable of binding with its complementary sbp member, and (b) the complementary sbp member. At least one of the sbp members is bound to a member of a signal producing system. In a preferred embodiment, at least one of the reversibly confined sbp members is bound to at least one member of a signal producing system. Alternatively, the complementary sbp member can be bound to a member of the signal producing system. Additionally, the present invention also includes a composition obtained by evaporative removal of the liquid from the above described composition.

The composition of the encapsulating material may vary widely. Preferably the encapsulating material is a liposome. The liposome is preferably composed of phospholipids or phospholipid mixtures found in natural membranes including lecithin, or synthetic glyceryl phosphate diesters of saturated or unsaturated 12 to 24 carbon linear fatty acids wherein the phosphate can be present as a monoester, or as an ester of a polar alcohol such as ethanolamine, choline, inositol, serine, glycerol and the like. Particularly preferred phospholipids include L-α-palymitoyl oleoylphosphatidylcholine (POPC), L-α-palmitoyl oleoylphosphatidylglycerol (POPG), L-α-dioleoyl-phosphatidylglycerol, and L-α-(dioleoyl)-phosphatidyl ethanolamine. Phospholipid substitutes may also be used. Other amphiphytic compounds that have a polar head group, usually charged, and a hydrophobic portion usually comprised of two or more linear hydrocarbon chains. Examples of phospholipid substitutes include dicetylphosphate, dialkoxypropylphosphates wherein the alkyl groups have linear chains of 12-20 carbon atoms, DOTMA, sphingomyelin, cardiolipin, and the like. The lipid material can also include cholesterol and its derivatives.

In a preferred embodiment the composition of the liposomes is 67–97% POPC, 3–30% POPG and 0–30% cholesterol. Illustrative of such a liposome is 67%

POPC, 4% POPG and 29% cholesterol. Another example is 70% POPC and 30% POPG. A further example is 76% POPC, 4% POPG and 20% cholesterol.

In one embodiment of the present invention the reversibly confined member is a conjugate of an enzyme and a hapten, the complementary member is antibody for the hapten, and the confining material is a liposome. Such a composition may further comprise stabilizers, other members of the signal producing system including the enzyme substrate. In such a case, the reversibly confined member can be glucose-6-phosphate dehydrogenase-theophylline, and the complementary member anti-theophylline.

Alternatively, the reversibly confined member is antibody, the complementary member is a conjugate of an enzyme and a hapten and the confining material is a liposome.

As a matter of convenience, the reagents for conducting an assay can be provided in a kit in package combination in predetermined amounts for use in assaying an analyte. The kit can comprise at least one sbp member reversibly confined in a material rendering the sbp member temporarily incapable of binding with its complementary sbp member and (b) the complementary sbp member. At least one of the sbp members is bound to a member of a signal producing group. The kit can also contain reagents for generating a signal in relation to the amount of analyte in the sample. Furthermore, the kit can comprise an agent for reversing the confinement of the confined sbp member. Ancillary agents can be included as necessary.

EXPERIMENTAL

The following examples are offered by way of illustration and not by way of limitation.

All temperatures not otherwise indicated are centigrade. Percents and parts not otherwise indicated are by weight, except for mixtures of liquids, which are by volume.

The following abbreviations are used: G6PDH-glucose-6-phosphate dehydrogenese; POPC-palmitoyl oleoylphosphatidylcholine; POPG-palmitoyl oleoylphosphatidylglycerol; RSA-rabbit serum albumin; BSA-bovine serum albumin; G6P-glucose-6-phosphate; NAD-nicotinamide adenine dinucleotide; Triton-Triton X-100; Buffer-0.055M Tris-Cl, pH 8, containing 0.05% sodium azide; 1 Eu=0.003 $\Delta A^{1cm}{}_{34nm}$.

EXAMPLE 1

Liposome Characterization and Preparation

Enzyme and enzyme-hapten conjugates were concentrated to 5 mg/ml prior to encapsulation. Antibody was used undiluted. All proteins were dialyzed against Buffer, prior to encapsulation.

The lipids were combined in a glass vial in chloroform solution. Chloroform was removed under a gentle stream of nitrogen. Traces of solvent were removed under high vacuum for more than 4 hours. The lipid was then dissolved at 30 mg/ml in t-butanol at 60° with gentle stirring. The butanol solution was freeze-dried to give a bulky, fluffy powder which was kept dry and cold (−20° C.) until used.

Method 1. Protein solution (1 ml per 100 mg phospholipid) was added at ambient temperature to the lipid and mixed by vortex. A volume of buffer equal to twice that of the protein was added and the suspension again vortex mixed to give a thick, milky suspension of liposomes with no unsuspended lipid or lumps. The suspension was then diluted with buffer to 20 times the original protein volume. Liposomes were collected by centrifugation at 15K rpm for twenty minutes at 4°. The supernatant was removed by aspiration and retained for determination of encapsulated protein. The liposome pellet was separated from supernatant shortly after centrifugation. The liposomes were washed twice with a buffer twenty times the volume of the original protein volume. Thereafter the liposomes were resuspended by shaking. Liposomes were repelleted by centrifugation and the supernatant removed. The washed liposomes were suspended in twenty times the original protein volume.

Method 2. Protein was dissolved in Buffer (pH 7). A liposome suspension was produced by vortex mixing lipid powder and protein. The unpurified suspension was diluted with 1 volume of Buffer and filtered through a succession of Nucleopore polycarbonate filters with progressively smaller pores (1.0μ, 0.6μ., 0.4μ, and 0.2μ). The filtration through the 0.2μ filter was repeated three times. The membrane was attached to a manually operated syringe to effect the filtration. A filter of 13 mm diameter was used. During the filtration, the light scattering properties of the liposomes were visibly changed, reflecting their decreased size. Finally, the small liposomes were purified by gel filtration over 30×1.5 cm column of Sephacryl S-1000. The column was eluted with Buffer at 30 ml/hr and fractions of 1 ml collected. The liposomes emerged as an asymmetric peak with a long trailing edge preceding the peak of unencapsulated protein. Fractions were assayed with and without Triton X-100. Liposomes were pooled so as to exclude any unencapsulated protein.

It is an important feature of Method 2 that the membrane filtration occurs in the presence of undiluted protein so that as the liposomes break there is no net loss of encapsulated protein.

When liposomes encapsulating a theophylline-G6PDH conjugate were made by Method 1, enzyme activity was as follows:

|  | % of Input Activity |
|---|---|
| Unpurified liposome preparation | 98.7 |
| Encapsulated in liposomes | 28.4 |
| Unencapsulated | 70.1 |
| Recovery (encapsulated + unencapsulated) after purification of liposomes | 98.5 |
| Latency of enzyme in liposomes | 99% |

The act of preparing the liposomes caused a very small loss of activity. Almost all the enzyme was recovered in the purified liposomes and the original liposome supernatant. About one-third of the activity was encapsulated in nonleaky liposomes. Results with other enzyme conjugates were similar.

Method 1 is applicable to both G6PDH-hapten conjugates and antibodies. It was used to encapsulate native G6PDH and its digoxin, theophylline, quinidine and thyroxine conjugates with comparable degrees of encapsulation and latency. Both polyclonal and monoclonal antibodies and a complex of enzyme and antibody (anti-enzyme) were also encapsulated.

EXAMPLE 2

Enzyme Activity Measurement

Theophylline-G6PDH was encapsulated in liposomes (POPC, 67%; POPG, 4%; Cholesterol, 29%) as in Method 1 above and suspended in Buffer (25 mg lipid/ml). G6P (0.13M), NAD (0.08M), and RSA (20 mg/ml) in buffer (pH 4.7) were prepared as a substrate. Encapsulated enzyme (50 μl) and substrate (50 μl) were mixed with 0.8 ml of buffer with and without the addition of Triton (5%). $\Delta A_{340}$ at 30° was recorded over 30 seconds in a temperature regulated cell beginning when the temperature was reached. In the absence of Triton the enzyme containing liposomes exhibited essentially no activity (less than 1%). In the presence of Triton most of the encapsulated enzyme was released within 30 seconds.

EXAMPLE 3

Assay using Encapsulated Digoxin-G6PDH as a Single Liquid Reagent

The lipid composition prepared in Example 1 above was used in an assay for digoxin. The assay employed the following reagents:

TABLE 1

| Reagent: | Digoxin-G6PDH encapsulated in liposomes (POPC 70%, POPG 30%) (0.49 mg lipid/ml,) Anti-digoxin optimized for response, 0.13M G6P, RSA (20 mg/ml) in buffer |
|---|---|
| Diluent: | 0.5% Triton, 4 mM NAD, 5mM NaN$_3$, 0.005% Thimerosal, pH 4.4 |

Protocol: 50 μl of the reagent was drawn up into a diluter and dispensed with 200 μl of buffer containing RSA (1 mg/ml) into a 1 ml Croan cup. A 50 μl aliquot of the sample was drawn up and dispersed with 700 μl of diluent into the Croan cup. Immediately after sample addition, the entire sample was aspirated into a flow cell and readings were taken at 30° over thirty seconds. The results are reported in EMIT assay units (EU) in Table 2.

TABLE 2

| Digoxin (μg/ml) | Two Reagent | Single Reagent |
|---|---|---|
| 0 | 386 | 369 |
| 0.083 | 410 | 403 |
| 0.166 | 456 | 440 |
| 0.333 | 518 | 511 |
| 0.666 | 603 | 584 |
| 1.33 | 645 | 628 |
| 2.66 | 678 | 653 |
| 5.33 | 713 | — |
| 10.65 | 717 | 665 |

Sufficient anti-digoxin antibody was present to cause 46% inhibition of digoxin-G6PDH, but no inhibition occurred until Triton was added.

EXAMPLE 4

Comparison Assay Using Two Separate Liquid Reagents

As a comparison to the assay using a single liquid reagent an assay was run using unencapsulated enzyme conjugate and antibody in separate liquid reagents. The reagent quantities and the final volume of the assay were arranged to be identical to those in the single reagent assay above in Example 3.

The assay employed the following reagents:

TABLE 3

| Reagent A: | Digoxin-G6PDH (conc. determined to give same rate, i.e. when no anti-digoxin, as in Example 3 above), 0.13M G6P, RSA (20 mg/ml) in buffer. |
|---|---|
| Reagent B: | Anti-digoxin (Conc. determined to give same final quantity as in Example 3 above), 0.13M G6P, RSA (20 mg/ml) in buffer. |

Protocol 50 μl of Reagent A was drawn up into a diluter and suspended with 100 μl of buffer containing RSA (1 mg/ml into a Croan cup. A 50 μl aliquot of sample diluted with 100 μl buffer containing RSA (1 mg/ml) and added to the Croan cup. 25 μl of Reagent B was drawn up into a diluter and dispensed with 700 μl of buffer into the Croan cup. Immediately thereafter, the sample was assayed as in Example 3 above. The results are reported in EMIT assay units in Table 2.

EXAMPLE 5

Assay using Encapsulated Theophylline-G6PDH as a Single Liquid Reagent

Theophylline-G6PDH was encapsulated in liposomes (POPC 76%, POPG 4%, and cholesterol 20%) and used in an assay for theophylline. The assay employed the following reagents:

TABLE 4

| Reagent: | Theophylline-G6PDH encapsulated in liposome (POPC 76%, POPG 4%, cholesterol 20%) 0.86 μg/ml monoclonal anti-theophylline, 3.0 mM NAD, and BSA (2 mg/ml) in buffer. |
|---|---|
| Diluent: | 2.5% Triton, 2% sodium deoxycholate 3 mM G6P, 1 mg/ml BSA, 50 mM NaN$_3$. |

Protocol 0.3 ml of the Reagent dispensed into a Croan cup. A 8.3 μl serum sample was drawn up into a diluter and dispensed into the Croan cup together with 0.6 ml of diluent.

Immediately after sample addition the entire sample was aspirated into a flow cell and enzyme activity was measured at 30° (fifteen seconds delay, thirty second read). The results are reported in EMIT assay units in Table 5.

TABLE 5

| Theophylline (μg/ml) | Single Reagent (Eu) |
|---|---|
| 0 | 310 |
| 2.5 | 356 |
| 5 | 394 |
| 10 | 455 |
| 20 | 537 |
| 40 | 610 |

EXAMPLE 6

Assay Using Encapsulated and Free Anti-G6PDH

Anti-G6PDH was encapsulated in liposome. The liposome composition was L-α-dioleoyl lecithin (70%) and L-α-dioleoyl phosphatidyl glycerol (30%).

TABLE 4

| | |
|---|---|
| Enzyme: | G6PDH, dissolved in buffer containing RSA (1 mg/ml) |
| Encapsulated Antibody: | Anti-G6PDH, in liposomes (70% L-α-(dioleoyl) lecithin and 30% L-α-dioleoylphosphatidyl glycerol), suspended in buffer containing RSA (1 mg/ml) |
| Free Antibody: | Anti-G6PDH, in buffer containing RSA (1 mg/ml) |
| Substrate: | 0.13M G6P, 0.08M NAD, and RSA (20 mg/ml) in buffer (pH 4.7) |

Protocol: 50 μl of enzyme (270 ng) was mixed with 50 μl of free or encapsulated antibody and 0.6 ml Buffer containing (1 mg/ml) with or without 5% Triton. After one hour at ambient temperature, 50 μl of substrate was added together with 0.3 ml buffer. The assay was read as in Example 2 above and the result are reported in EMIT assay units in Table 7.

TABLE 7

| Antibody | Triton | EMIT Units | % Inhibition |
|---|---|---|---|
| Absent | Absent | 542 | 0 |
| Absent | Present | 544 | 0 |
| Free[1] | Absent | 238 | 56 |
| Free[1] | Present | 245 | 55 |
| Encapsulated[2] | Absent | 510 | 6 |
| Encapsulated[2] | Present | 233 | 57 |

[1] 7 nL undiluted γ-globulin fraction.
[2] 9.3 μg lipid.

Data showed that encapsulated antibody inhibited the enzyme much less than the same amount of unencapsulated antibody. Triton added to release encapsulated antibody did not affect either enzyme activity or extent of inhibition in enzyme by antibody. The encapsulated antibody mixed with enzyme caused 57% inhibition in the brief assay time when Triton was added, but caused only 6% inhibition in 1 hour in the absence of Triton.

EXAMPLE 7

Alternative Releasing Agents

Theophylline-G6PDH was encapsulated in liposomes (POPC, 58%; POPG, 25%; and Cholesterol, 17%) and suspended at 5 mg lipid/ml in buffer.

TABLE 9

| Additive | Treatment | Activity Recovered % | Enzyme Act. Unencap. % | Act. Release |
|---|---|---|---|---|
| — | — | (100) | 2 | 0 |
| RSA (45 mg/ml) in buffer | Freeze/ thaw | 92 | 34 | 32 |
| Water | — | 100 | 10 | 8 |
| — | Sonicate | 95 | 33 | 31 |
| Triton | — | 100 | 0 | 100 |

1 ml of the encapsulated theophylline-G6PDH was mixed with the additive and subjected to the treatments as shown in Table 9. Thereafter 0.1 ml aliquots were diluted with 0.9 ml buffer containing RSA (1 mg/ml). 50 μl aliquots of the diluted samples were assayed as in Example 4 with or without 2% Triton. The fraction of enzyme activity recovered and the fraction unencapsulated after treatment were then calculated and are shown in Table 9.

The present invention provides for compositions which allow rapid, simple tests for determining a wide variety of analytes. The single liquid reagent provides a high degree of reliability and accuracy and can be used easily by personnel with a low level of skill and/or training. There is no need to reconstitute a powder, and no need to mix various reagents to obtain accurate proportions. Conventional equipment can be employed and two tests can be carried out simultaneously, e.g., a control and the sample, so that the conditions for the two assay-media are the same.

Although the foregoing invention has been described in some detail by way of illustration and example for purposes of clarity of understanding, it will be obvious that certain changes and modifications may be practiced within the scope of the appended claims.

What is claimed is:

1. An assay method for determining an analyte in a sample suspected of containing the analyte wherein the analyte is a member of a specific binding pair (sbp) consisting of ligand and its complementary receptor and wherein a signal producing system is employed which provides a detectable signal in relation to the amount of analyte in said sample, said assay method comprising the steps of
   a) combining a sample suspected of containing an analyte with a composition comprising in a single liquid medium (1) at least one sbp member reversibly confined in a gel rendering said sbp member incapable of binding with its complementary sbp member until such confinement is reversed wherein said outer surface of said gel is essentially free of said sbp members, and (2) said complementary sbp member wherein at least one of said sbp members is bound to a member of a signal producing system; and
   b) providing means for reversing the confinement of said sbp member from said gel; and
   c) measuring a signal produced in relation to the amount of analyte in said sample.

2. The method according to claim 1 wherein said means chemically reverses said confinement.

3. The method according to claim 1 wherein at least one of said reversibly confined sbp members is bound to a member of the signal producing system.

4. The method according to claim 1 wherein the member of said signal producing system is selected from the group consisting of enzymes, co-enzymes, fluorescers, dyes, enzyme substrates, chemiluminescers, and enzyme co-factors.

5. The method according to claim 1 wherein the member of the signal producing system is an enzyme.

6. The method according to claim 5 wherein the member of the signal producing system is glucose-6-phosphate dehydrogenase.

7. The method according to claim 1 wherein said sbp members are members of an immunological pair (mip) consisting of antigen and antibody.

8. The method according to claim 1 wherein said analyte is selected from the group consisting of antigens and antibodies.

9. The method according to claim 1 wherein said analyte is selected from the group consisting of drugs, polypeptides, nucleic acids and polysaccharides.

10. The method according to claim 9 wherein said drugs are selected from the group consisting of theophylline, thyroxine and digoxin.

11. The method according to claim 1 wherein said means for reversing the confinement of said sbp member is a chemical means or a physical means or a combination thereof.

12. The method according to claim 11 wherein said means is a chemical means selected from the group consisting of detergents and organic solvents.

13. The method according to claim 11 wherein said means is a physical means selected from the group consisting of a change in temperature, sonication and osmotic shock.

14. The method according to claim 1 wherein said reversibly confined member is a conjugate of an enzyme and a hapten and said complementary member is an antibody for said hapten.

15. The method according to claim 1 wherein said reversibly confined member is antibody and said complementary member is a conjugate of an enzyme and a hapten.

16. The method according to claim 14 or 15 wherein said enzyme is glucose-6-phosphate dehydrogenase.

17. The method according to claim 1 wherein said reversibly confined member is a conjugate of glucose-6-phosphate dehydrogenase-theophylline, said complementary sbp member is anti-theophylline.

18. The method according to claim 1 wherein said composition further comprises at least one additional member of said signal producing system.

19. An assay method for determining an analyte in a sample suspected of containing the analyte wherein the analyte is a member of a specific binding pair (sbp) consisting of ligand and its complementary receptor and wherein a signal producing system is employed which provides a detectable signal in relation to the amount of analyte in said sample, said assay method comprising the steps of
   a) combining a sample suspected of containing an analyte with a composition comprising in a single liquid medium (1) at least one sbp member reversibly confined in a gel rendering said sbp member incapable of binding with its complementary sbp member until such confinement is reversed, and (2) said complementary sbp member wherein at least one of said sbp members is bound to a member of a signal producing system; and
   b) providing means for reversing the confinement of said sbp member from said gel; and
   c) measuring a signal produced in relation to the amount of analyte in said sample.

20. The method according to claim 19 wherein said means chemically reverses said confinement.

21. The method according to claim 19 wherein at least one of said reversibly confined sbp members is bound to a member of the signal producing system.

22. The method according to claim 19 wherein the member of said signal producing system is selected from the group consisting of enzymes, co-enzymes, fluorescers, dyes, enzyme substrates, chemiluminescers, and enzyme co-factors.

23. The method according to claim 19 wherein the member of the signal producing system is an enzyme.

24. The method according to claim 23 wherein the member of the signal producing system is glucose-6-phosphate dehydrogenase.

25. The method according to claim 19 wherein said sbp members are members of an immunological pair (mip) consisting of antigen and antibody.

26. The method according to claim 19 wherein said analyte is selected from the group consisting of antigens and antibodies.

27. The method according to claim 19 wherein said analyte is selected from the group consisting of drugs, polypeptides, nucleic acids and polysaccharides.

28. The method according to claim 27 wherein said drugs are selected from the group consisting of theophylline, thyroxine and digoxin.

29. The method according to claim 19 wherein said means for reversing the confinement of said sbp member is a chemical means or a physical means or a combination thereof.

30. The method according to claim 29 wherein said means is a chemical means selected from the group consisting of detergents and organic solvents.

31. The method according to claim 29 wherein said means is a physical means selected from the group consisting of a change in temperature, sonication and osmotic shock.

32. The method according to claim 29 wherein said reversibly confined member is a conjugate of an enzyme and a hapten and said complementary member is antibody for said hapten.

33. The method according to claim 29 wherein said reversibly confined member is antibody and said complementary member is a conjugate of an enzyme and a hapten.

34. The method according to claim 32 or 33 wherein said enzyme is glucose-6-phosphate dehydrogenase.

35. The method according to claim 19 wherein said reversibly confined member is a conjugate of glucose-6-phosphate dehydrogenase-theophylline and said complementary sbp member is anti-theophylline.

36. The method according to claim 19 wherein said composition further comprises at least one additional member of said signal producing system.

37. A composition for conducting an assay for an analyte which is a member of a specific binding pair (sbp) consisting of ligand and its complementary receptor, said composition comprising in a single liquid medium:
   (a) at least one sbp member reversibly confined in a gel rendering said sbp member incapable of binding with its complementary sbp member until such confinement is reversed; and
   (b) said complementary sbp member; wherein at least one of said sbp members is bound to a member of a signal producing system.

38. The composition according to claim 37 wherein at least one of said reversibly confined sbp members is bound to a member of a signal producing system.

39. A composition obtained by evaporative removal of the liquid from the composition of claim 37.

40. The composition according to claim 37 wherein said sbp members are selected from the group consisting of antibodies and antigens.

41. The composition according to claim 37 wherein said member of said signal producing system is selected from the group consisting of enzymes, co-enzymes, fluorescers, dyes, enzyme substrates, chemiluminescers, and enzyme co-factors.

42. The composition according to claim 37 wherein the member of the signal producing system is an enzyme.

43. The composition according to claim 37 wherein said member of said signal producing system is glucose-6-phosphate dehydrogenase.

44. The composition according to claim 37 wherein said reversibly confined member is a conjugate of an enzyme and a hapten and said complementary member is antibody for said hapten.

45. The composition according to claim 37 wherein said reversibly confined member is antibody and said complementary member is a conjugate of an enzyme and a hapten.

46. The composition according to claims 44 or 45 wherein said enzyme is glucose-6-phosphate dehydrogenase.

47. The composition according to claim 37 wherein said reversibly confined member is glucose-6-phosphate dehydrogenase-theophylline and said complementary member is anti-theophylline.

48. The composition according to claim 37 further comprising other members of said signal producing system.

49. A kit for use in an assay comprising in combination:
(a) a composition according to claim 37; and
(b) a reagent for reversing the confinement of the confined sbp member.

50. A kit for use in an assay comprising in combination:
(a) a composition according to claim 44; and
(b) a reagent for reversing the confinement of said confined member.

51. A kit for use in an assay comprising in combination:
(a) a composition according to claim 45; and
(b) a reagent for reversing the confinement of said confined member.

52. A kit for use in an assay comprising in combination:
(a) a composition according to claim 47; and
(b) a reagent for reversing the confinement of said confined member.

53. The kit according to claim 49, 50, 51 or 52 wherein said reagent is selected form the group consisting of detergents and organic solvents.

54. In an assay for determining an analyte in a sample suspected of containing the analyte wherein the analyte is a member of a specific binding pair (sbp) consisting of ligand and its complementary receptor and wherein a signal producing system is employed which provides a detectible signal in relation to the amount of analyte in the sample, said assay comprising the steps of (a) providing in combination said sample, an sbp member, and a complementary sbp member, wherein at least one of said sbp members is bound to a member of said signal producing system and (b) detecting a signal in relation to the presence of analyte in said sample, the improvement comprising employing as a reagent in said assay a composition comprising in a single liquid medium (1) at least one sbp member reversibly confined in a gel rendering said sbp member incapable of binding with its complementary sbp member until such confinement is reversed and (2) said complementary sbp member.

55. An assay method for determining an analyte in a sample suspected of containing the analyte wherein the analyte is a member of a specific binding pair (sbp) consisting of ligand and its complementary receptor and wherein a signal producing system is employed which provides a detectable signal in relation to the amount of analyte in said sample, said assay method comprising the steps of a) combining a sample suspected of containing an analyte with a composition comprising in a single liquid medium (1) a sbp member which is a conjugate of an enzyme and a hapten which together with a stablizing agent for said enzyme are reversibly confined in a particulate material selected from gels rendering said sbp member incapable of binding with its complementary sbp member until such confinement is reversed, and (2) said complementary sbp member which is antibody for said hapten; and b) providing means for reversing the confinement of said sbp member from said particulate material; and c) measuring a signal produced in relation to the amount of analyte in said sample.

56. The method according to claim 55 wherein said means chemically reverses said confinement.

57. The method according to claim 55 wherein the enzyme is glucose-6-phosphate dehydrogenase.

58. The method according to claim 55 wherein said means for reversing the confinement of said sbp member is a chemical means or a physical means or a combination thereof.

59. The method according to claim 58 wherein said means is a chemical means selected from the group consisting of detergents and organic solvents.

60. The method according to claim 58 wherein said means is a physical means selected from the group consisting of a change in temperature, sonication and osmotic shock.

61. The method according to claim 59 or 60 wherein said enzyme is glucose-6-phosphate dehydrogenase.

62. The method according to claim 55 wherein said reversibly confined sbp member is a conjugate of glucose-6-phosphate dehydrogenase-theophylline and said antibody is anti-theophylline.

63. A composition for conducting an assay for an analyte which is a member of a specific binding pair (sbp) consisting of ligand and its complementary receptor, said composition comprising in a single liquid medium:
(a) a sbp member which is a conjugate of an enzyme and a hapten which together with a stabilizing agent for said enzyme are reversibly confined in a particulate material selected from gels rendering said sbp member incapable of binding with its complementary sbp member until such confinement is reversed;
(b) a complementary sbp member which is antibody for said hapten.

64. A composition obtained by evaporative removal of the liquid from the composition of claim 63.

65. The composition according to claim 63 wherein said enzyme is glucose-6-phosphate dehydrogenase.

66. The composition according to claim 63 wherein said reversibly confined sbp member is glucose-6-phosphate dehydrogenase-theophylline and said antibody is anti-theophylline.

67. A kit for use in an assay comprising in combination:
(a) a composition according to claim 63; and
(b) a reagent for reversing the confinement of the confined sbp member.

68. A kit for use in an assay comprising in combination:
(a) a composition according to claim 6; and
(b) a reagent for reversing the confinement of said confined member.

69. In an assay for determining an analyte in a sample suspected of containing the analyte wherein the analyte is a member of a specific binding pair (sbp) consisting of ligand and its complementary receptor and wherein a signal producing system is employed which provides a detectible signal in relation to the amount of analyte in the sample, said assay comprising the steps of (a) providing in combination said sample, an sbp member, and a complementary sbp member, wherein at least one of said sbp members is bound to a member of said signal producing system and (b) detecting a signal in relation to the presence of analyte in said sample, the improvement comprising employing as a reagent in said assay a composition comprising in a single liquid medium (1) a sbp member comprising a conjugate of an enzyme and a hapten which together with a stabilizing agent for said enzyme are reversibly confined in a particulate material selected from the group of gels rendering said sbp member incapable of binding with its complementary sbp member until such confinement is reversed and (2) said complementary sbp member.

70. A method for conducting an assay for an analyte selected from the group consisting of theophylline, thyroxine and digoxin in a sample wherein said analyte is a member of a specific binding pair (sbp) consisting of ligand and its complementary receptor and wherein a signal producing system is employed which provides a detectable signal in relation to the amount of analyte in said sample, said method comprising (a) combining in a single liquid medium (i) a labeled sbp member comprising a hapten selected from the group consisting of theophylline, thyroxin and digoxin bound to the enzyme glucose-6-phosphate dehydrogenase reversibly confined in a gel rendering said sbp member incapable of binding to its complementary sbp member until such confinement is reversed wherein said outer surface of said gel is essentially free of said sbp members, (ii) said complementary sbp member which is an antibody and (iii) the sample;

(b) providing means for reversing the confinement of said sbp member from said gel; and (c) measuring the signal produced in relation to the amount of analyte in said sample.

71. The method according to claim 70 wherein said means for reversing the confinement of said sbp member is a chemical compound selected from the group consisting of TRITON, sodium deoxycholate, octylglucoside and sodium dodecylsulfate.

* * * * *